(12) United States Patent
Devcic

(10) Patent No.: US 10,620,243 B2
(45) Date of Patent: Apr. 14, 2020

(54) RECHARGEABLE BATTERY VOLTAGE ADAPTION

(71) Applicant: Cochlear Limited, Macquarie University, NSW (AU)

(72) Inventor: Josip Devcic, Hurstville (AU)

(73) Assignee: COCHLEAR LIMITED, Macquarie University, NSW (AU)

( * ) Notice: Subject to any disclaimer, the term of this patent is extended or adjusted under 35 U.S.C. 154(b) by 115 days.

(21) Appl. No.: 15/428,235

(22) Filed: Feb. 9, 2017

(65) Prior Publication Data

US 2018/0221662 A1 Aug. 9, 2018

(51) Int. Cl.
| A61N 1/05 | (2006.01) |
| G01R 21/133 | (2006.01) |
| A61N 1/36 | (2006.01) |
| H02J 7/00 | (2006.01) |

(52) U.S. Cl.
CPC ......... *G01R 21/133* (2013.01); *A61N 1/0541* (2013.01); *A61N 1/36036* (2017.08); *A61N 1/36038* (2017.08); *H02J 7/0063* (2013.01); *H02J 7/0078* (2013.01); *H02J 2007/0067* (2013.01)

(58) Field of Classification Search
None
See application file for complete search history.

(56) References Cited

U.S. PATENT DOCUMENTS

| 4,532,930 | A | * | 8/1985 | Crosby .............. A61N 1/36036 607/57 |
| 5,733,313 | A | | 3/1998 | Barreras, Sr. et al. |
| 6,140,801 | A | | 10/2000 | Aoki et al. |
| 6,342,774 | B1 | | 1/2002 | Kreisinger et al. |
| 6,922,591 | B2 | | 7/2005 | Single |
| 7,167,756 | B1 | | 1/2007 | Torgerson et al. |
| 7,853,813 | B2 | | 12/2010 | Lee |
| 2002/0076071 | A1 | | 6/2002 | Single |
| 2005/0046400 | A1 | | 3/2005 | Rotem |
| 2008/0307243 | A1 | * | 12/2008 | Lee ........................ G06F 1/3203 713/320 |
| 2013/0103114 | A1 | * | 4/2013 | Single ................... H02J 7/0075 607/57 |
| 2014/0167656 | A1 | * | 6/2014 | Yamada .................... H02J 7/00 318/139 |

(Continued)

OTHER PUBLICATIONS

International Search Report and Written Opinion in corresponding International Application No. PCT/IB2018/050564, dated May 11, 2018, 12 pages.

(Continued)

*Primary Examiner* — Ankit D Tejani
(74) *Attorney, Agent, or Firm* — Edell, Shapiro & Finnan, LLC

(57) ABSTRACT

Presented herein are techniques for adapting/adjusting the end-of-charge (termination) voltage of a rechargeable battery integrated in an auditory prosthesis or other electronic device based on an estimated power consumption of the auditory prosthesis or other electronic device. In particular, the estimated power consumption of an auditory prosthesis or other electronic device is used to set an end-of-charge voltage that is customized to the power consumption needs of the auditory prosthesis or other electronic device.

24 Claims, 6 Drawing Sheets

(56) References Cited

U.S. PATENT DOCUMENTS

| | | | |
|---|---|---|---|
| 2015/0196759 A1* | 7/2015 | Meskens | H04R 25/606 600/25 |
| 2015/0373463 A1* | 12/2015 | Palmer | A61N 1/37211 381/60 |
| 2017/0180874 A1 | 6/2017 | Goorevich et al. | |

OTHER PUBLICATIONS

PowerStream, "How does capacity correlate with charge voltage for lithium ion batteries?," http://www.powerstream.com/lithium-ion-charge-voltage.htm, Jan. 17, 2017, 3 pages.

\* cited by examiner

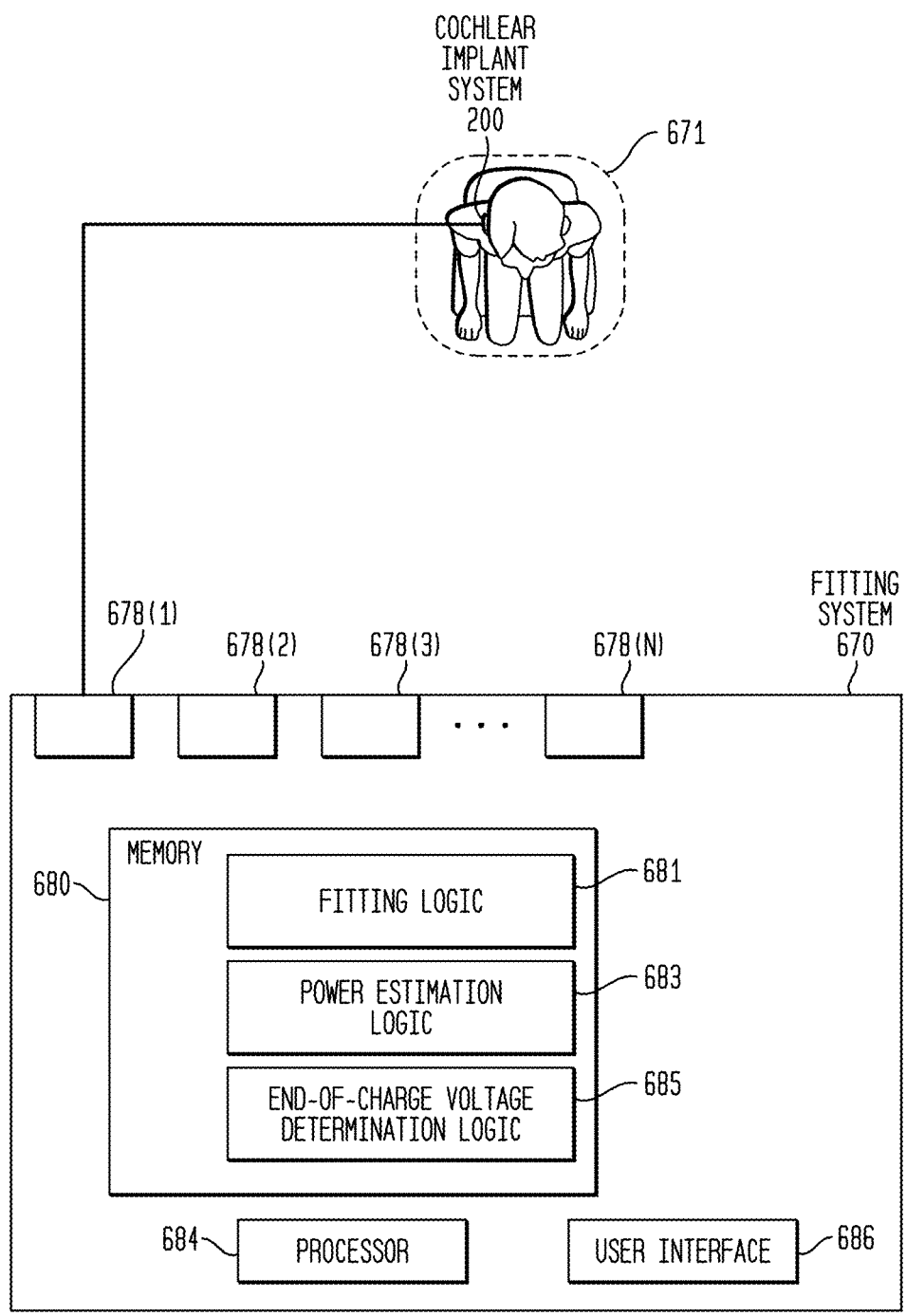

RECHARGEABLE BATTERY VOLTAGE ADAPTION

BACKGROUND

Field of the Invention

The present invention relates generally to implantable medical devices.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, auditory brainstem stimulators, cochlear implants, etc.), implantable pacemakers, defibrillators, functional electrical stimulation devices, and other implantable medical devices, have been successful in performing lifesaving and/or life-style enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process. Many of these functional components utilize power and/or data received from external components that are part of, or operate in conjunction with, the implantable medical device.

SUMMARY

In one aspect a method is provided. The method comprises: at an auditory prosthesis at least partially implanted in a recipient and comprising a rechargeable battery, obtaining information representative of an estimated power consumption of the auditory prosthesis; and setting an end-of-charge voltage of the rechargeable battery based on the estimated power consumption.

In another aspect an implantable medical device system is provided. The implantable medical device system comprises: an implantable medical device, comprising: a rechargeable battery; adaptive battery charging circuitry configured to charge the rechargeable battery; and a charge controller configured to set the adaptive battery charging circuitry based on an estimate of the operational power requirements of the implantable medical device.

In another aspect a method is provided. The method comprises: determining an estimated power consumption of an implantable medical device, wherein the implantable medical device includes an integrated rechargeable battery and adaptive battery charging circuitry; determining, based on the estimated power consumption of the implantable medical device, a selected termination voltage associated with charging of the rechargeable battery; and adjusting the adaptive battery charging circuitry so as to subsequently charge the rechargeable battery to the selected termination voltage.

BRIEF DESCRIPTION OF THE DRAWINGS

Embodiments of the present invention are described herein in conjunction with the accompanying drawings, in which:

FIG. 6 is a block diagram of a fitting system in accordance with embodiments presented herein.

DETAILED DESCRIPTION

Embodiments presented herein are generally directed to techniques for adapting/adjusting the charging voltage, sometimes referred to herein as the end-of-charge or termination voltage, of a rechargeable battery integrated in an auditory prosthesis or other electronic device based on an estimated power consumption of the auditory prosthesis or other electronic device. In particular, the estimated power consumption of an auditory prosthesis or other electronic device is used to set an end-of-charge voltage that is customized to the power consumption needs of the auditory prosthesis or other electronic device. in one embodiment, the end-of-charge voltage is set so as to provide sufficient capacity to provide a selected battery life (i.e., run-time) yet also improve the cycle life of the rechargeable battery (i.e., balance battery capacity and cycle life based on the needs of the specific recipient).

There are a number of different types of auditory prostheses or other electronic devices in which embodiments of the present invention may be implemented. However, merely for ease of illustration, the techniques presented herein are primarily described with reference to one type of auditory prosthesis, namely a cochlear implant. It is to be appreciated that the techniques presented herein may be used in many electronic devices, such as other partially or fully implantable medical device system now known or later developed, including other auditory prostheses (e.g., auditory brainstem stimulators, electro-acoustic hearing prostheses, bone conduction devices, bimodal hearing prostheses, etc.)

Figure 1:
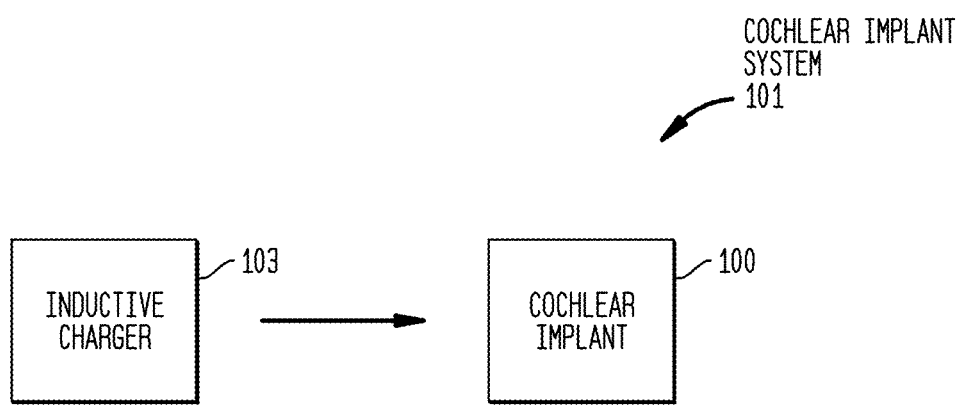
FIG. 1 is a block diagram illustrating a cochlear implant system in accordance with embodiments presented herein.

FIG. 1 is block diagram of an exemplary cochlear implant system 101 in which embodiments presented herein are implemented. The cochlear implant system 101 comprises a cochlear implant 100 and a charging component, sometimes referred to herein as an inductive charging station or inductive charger 103. The inductive charger 103 can have a number of different forms, such as a docking station, charging mat, etc.

As described below, the cochlear implant 100 comprises an integrated rechargeable battery (not shown in FIG. 1) that is configured to be recharged using power signals received from the inductive charger 103. Also as described below, the cochlear implant 100 includes a charge controller (not shown in FIG. 1) and adaptive battery charge circuitry (also not shown in FIG. 1) that are configured to set the end-of-charge voltage of the rechargeable battery based on a power consumption of the cochlear implant (operational power requirements of the cochlear implant). As used herein, the end-of-charge voltage of a rechargeable battery is the voltage level of the rechargeable battery that is attained at the end of a charging process, typically at a specified constant current. Termination of the charge process may be initiated when the end-of-charge voltage (i.e., the specified voltage level) has been reached.

Figure 2:
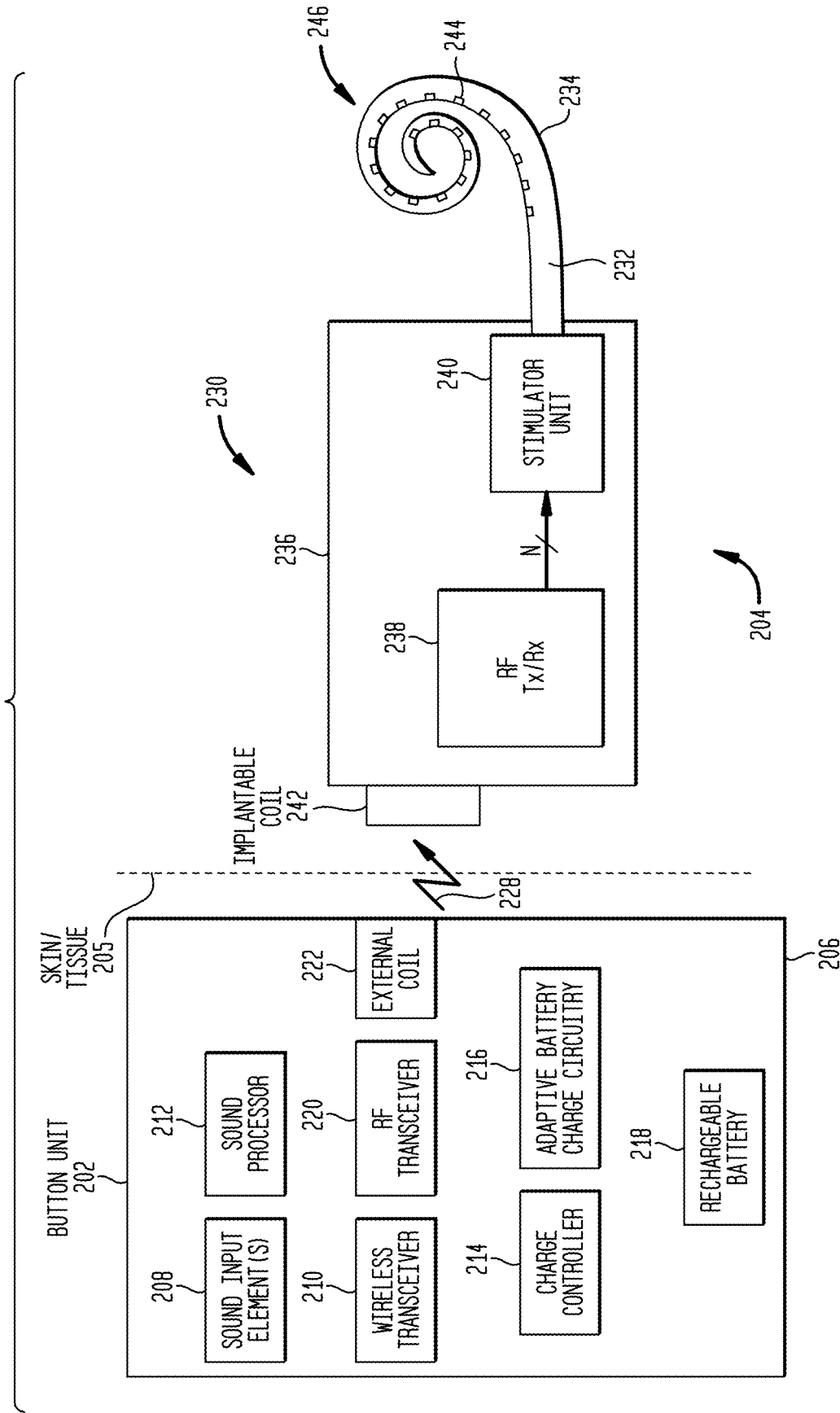
FIG. 2 is block diagram of a cochlear implant in accordance with embodiments presented herein.

Cochlear implant 100 of FIG. 1 can have any of a number of different arrangements. For example, FIG. 2 illustrates one example arrangement in which the cochlear implant, referred to as cochlear implant 200, comprises an external component 202 and an internal/implantable component 204. The external component 202 is configured to be directly or indirectly attached to the body of a recipient, while the implantable component 204 is configured to be subcutaneously implanted within the recipient (i.e., under the skin/tissue 205 of the recipient).

Traditionally, external components of a cochlear implant have been formed by two elements, a behind-the-ear unit and a separate coil unit that are connected by a cable. In these traditional arrangements, any sound input elements, sound processing elements, battery, etc. are housed in a behind-the-ear component, while the separate coil unit includes a radio-frequency (RF) coil for use in transcutaneous communication with the implantable component. However, in the example of FIG. 2, the external component 202 is a so-called "button" unit where the sound processing elements, battery, external coil, etc. are integrated into a single housing configured to be magnetically coupled to the recipient's head. As such, the button unit 202 includes a magnet (not shown in FIG. 2) and is configured to be worn at a location where this magnet can be magnetically coupled to an implantable magnet in the implantable component 204. Although FIG. 2 illustrates the external component 202 as a button unit, it is to be appreciated that embodiments presented herein may be implemented with external components having other arrangements, including behind-the-ear unit arrangements, in-the-ear arrangements, etc.

In the embodiment of FIG. 2, the button unit 202 comprises, among other elements, one or more sound input elements 208, a wireless receiver or transceiver 210, a sound processor 212, a charge controller 214, adaptive battery charge circuitry 216, a rechargeable battery 218 (e.g., a lithium ion rechargeable battery cell), a radio frequency (RF) transceiver unit (transceiver) 220, an external coil 222, and a magnet (not shown in FIG. 2) fixed relative to the external coil 222, that are all disposed in the same housing 206.

The one or more sound input elements 208 (e.g., microphones, audio input ports, telecoils, etc.) are configured to detect/receive input sound signals. The sound processor 212 executes one or more operations to convert signals received from the one or more sound input elements 208 and/or the wireless receiver 210 into output signals that represent electrical (current) stimulation for delivery to the recipient.

The sound processor 212 provides the output signals representative of the electrical stimulation to the RF transceiver 220. The RF transceiver 220 uses the external coil 222 to transmit the output signals, which are represented in FIG. 2 by arrow 228, to the implantable component 204 via a closely coupled radio frequency (RF) link (e.g., a 5 megahertz (MHz) inductive RF link).

In addition to the output signals, the RF transceiver 220 also uses the external coil 222 to transmit power to the implantable component 204. In certain embodiments, the external coil 222 is used to communicate with the implantable component 204 during certain periods of time and to receive power from an inductive charger (FIG. 1) to charge the battery 218 during other periods of time (i.e., the external coil may be a dual-use coil that both receives and transmits power signals).

The rechargeable battery 218 is configured to provide the energy needed to power the other elements of the cochlear implant 200, as well as to provide the current needed to electrically stimulate the recipient's cochlea. As described further below, the adaptive battery charge circuitry 216 is configured to operate under the control of the charge controller 214 so as to charge the rechargeable battery 218 to a selected end-of-charge voltage (i.e., to a selected voltage level). Also as described further below, the end-of-charge voltage of the rechargeable battery is set based on an estimated power consumption of the cochlear implant 200.

As noted, the cochlear implant 200 also includes the implantable component 204. The implantable component 204 comprises an implant body (main module) 230, a lead region 232, and an elongate intra-cochlear stimulating assembly 234. The implant body 230 generally comprises a hermetically-sealed housing 236 in which an internal RF transceiver unit (transceiver) 238 and a stimulator unit 240 are disposed. The implant body 230 also includes an internal/implantable coil 242 that is generally external to the housing 236, but which is connected to the RF transceiver 238 via a hermetic feedthrough (not shown in FIG. 2). Implantable coil 242 is typically a wire antenna coil comprised of multiple turns of electrically insulated single-strand or multi-strand platinum or gold wire. The electrical insulation of implantable coil 242 is provided by a flexible molding (e.g., silicone molding), which is not shown in FIG. 22. Generally, a magnet is fixed relative to the implantable coil 242 for magnetic coupling with the magnet in the button unit 202.

Elongate stimulating assembly 234 is configured to be at least partially implanted in the recipient's cochlea (not shown) and includes a plurality of longitudinally spaced intra-cochlear electrical stimulating contacts (electrodes) 244 that collectively form a contact array 246 for delivery of electrical stimulation (current) to the recipient's cochlea. Stimulating assembly 234 extends through an opening in the cochlea (e.g., cochleostomy, the round window, etc.) and has a proximal end connected to the stimulator unit 240 via the lead region 232 and a hermetic feedthrough (not shown in FIG. 2). Lead region 232 includes a plurality of conductors (wires) that electrically couple the electrodes 244 to the stimulator unit 240.

As noted, the output signals 228 are sent to the implantable component 204 via a closely-coupled RF link formed by the external coil 222 and the implantable coil 242. More specifically, the magnets fixed relative to the external coil 222 and the implantable coil 242 facilitate the operational alignment of the external coil 222 with the implantable coil 242. This operational alignment of the coils enables the external coil 222 to transmit the output signals 228, as well as power signals received from battery 218, to the implantable coil 242.

In general, the output signals 228 are received at the RF transceiver 238, decoded, and provided to the stimulator unit 240. The stimulator unit 240 is configured to utilize the signals received from the RF transceiver 238 to generate electrical stimulation signals (e.g., current signals) for delivery to the recipient's cochlea via one or more stimulating contacts 244. In this way, cochlear implant 200 electrically stimulates the recipient's auditory nerve cells, bypassing absent or defective hair cells that normally transduce acoustic vibrations into neural activity, in a manner that causes the recipient to perceive one or more components of the received sound signals.

As noted, FIG. 2 illustrates a cochlear implant having both external and implantable components. It is to be appreciated that the techniques presented herein may be implemented in totally implantable cochlear implants (i.e., cochlear implants where all components of the cochlear implant are configured to be implanted under the skin/tissue of a recipient). In these embodiments, elements shown as part of the button unit 202 of FIG. 2 are included in the implantable component.

Figure 3:
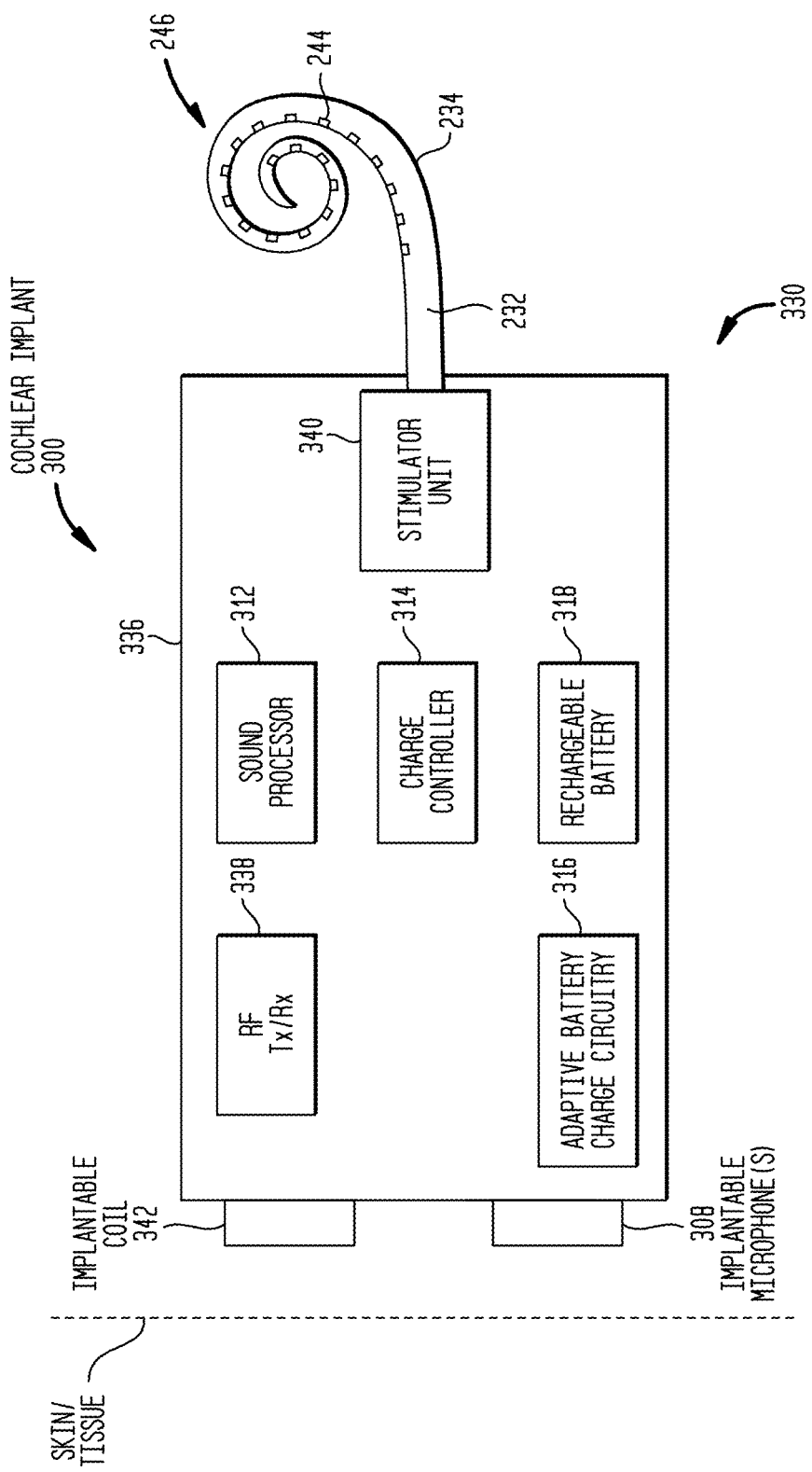
FIG. 3 is block diagram of another cochlear implant in accordance with embodiments presented herein.

For example, FIG. 3 is a block diagram of an exemplary totally implantable cochlear implant 300 configured to implement embodiments of the present invention. Because all components are implantable, cochlear implant 300 operates, for at least a finite period of time, without the need of an external device. Cochlear implant 300 includes an implant body (main module) 330, one or more implantable microphones 308, and an elongate intra-cochlear stimulating assembly 234 as described above with reference to FIG. 2. The microphone(s) 308 may be disposed in, or electrically connected to, the implant body 330. The implant body 330 comprises a hermetically-sealed housing 336 in which an internal RF transceiver unit (transceiver) 238, a sound processor 312, a charge controller 314, adaptive battery charge circuitry 316, a rechargeable battery 318, and a stimulator unit 340 are disposed.

The sound processor 312 is configured to execute sound processing and coding to convert received/detected sound signals (e.g., received by the one or more microphones 308) into output signals for use by the stimulator unit 340 in delivering electrical stimulation (current) to a recipient via electrodes 244.

The implant body 330 also includes an internal/implantable coil 342 that is generally external to the housing 336, but which is connected to the RF transceiver 338 via a hermetic feedthrough (not shown in FIG. 3). Generally, a magnet is fixed relative to the implantable coil 342.

The implantable coil 342 and the transceiver unit 338 enable cochlear implant 300 to receive signals from, and/or transmit signals to, external devices via a closely coupled RF link (e.g., a 5 MHz inductive RF link). For example, transceiver unit 338 may be configured to transcutaneously receive power and/or data from an external device.

The rechargeable battery 318 is configured to provide the energy needed to power the other elements of the cochlear implant 300, as well as to provide the current needed to electrically stimulate the recipient's cochlea. As described further below, the adaptive battery charge circuitry 316 is configured to operate under the control of the charge controller 314 so as to charge the rechargeable battery 318 to a selected end-of-charge voltage. Also as described further below, the end-of-charge voltage of the rechargeable battery is set based on an estimated power consumption of the cochlear implant 300.

As noted above, FIGS. 2 and 3 illustrate two suitable configurations of medical devices that can implement the techniques described herein. It is to be appreciated that these two arrangements are illustrative, and that the techniques described herein can be implemented in any of a variety of other medical device configurations and/or other contexts (i.e., embodiments presented herein are not limited to cochlear implants with button units, totally implantable cochlear implants, etc.)

As noted above, cochlear implants 200 and 300 of FIGS. 2 and 3, respectively, each include a respective rechargeable battery 218, 318. The rechargeable batteries 218 and 318 are used to power the other elements of the respective cochlear implant 200 and 300, as well as provide the current needed to electrically stimulate the recipient's cochlea. Cochlear implants are increasingly progressing towards the use of integrated rechargeable batteries (e.g., rechargeable monolithic battery cells) that are not user replaceable, due to as a result of the device design, location of the battery (e.g., within the recipient, thus requiring a surgical procedure to remove the battery), etc.

The total amount of energy a battery can store at any one time, often measured in terms of Milliampere Hours (mAh), is referred to herein as the "capacity" of the battery. The "cycle life" of a rechargeable battery refers to the number of complete charge/discharge cycles that the battery is able to support before the capacity of the battery falls below some threshold of its original capacity so as be insufficient for its intended purpose (e.g., under 50% of the original battery capacity). With the increasing use of monolithic or integrated batteries, the lifetime of a cochlear implant, or a component thereof, may be determined by the cycle life of the battery. That is, if the rechargeable battery is integrated within a component of a cochlear implant and completely non-replaceable, then at least the component that includes the battery may need to be replaced once the cycle life of the battery has been reached.

The actual power requirements of cochlear implants can greatly vary from recipient to recipient and may not be known until after the cochlear implant has been implanted in a specific recipient. As a result, the capacity of rechargeable batteries used in cochlear implants may be selected based on a worst case use by any recipient in a single day, as the recipient would not be able to exchange the battery throughout the day. That is, it is generally assumed that a recipient has the ability to charge his/her rechargeable battery at night and, as such, the goal is to provide a recipient with approximately one full day of operation on a single battery charge (i.e., a fully charged battery should power the cochlear implant for at least approximately 14-16 hours without the need to recharge the battery). However, the inventors of the embodiments described herein have determined that the worst case capacity is only needed for a minority of recipients and that a large percentage of recipients would be able to achieve a single day of operation with a lower battery capacity.

Figure 4:
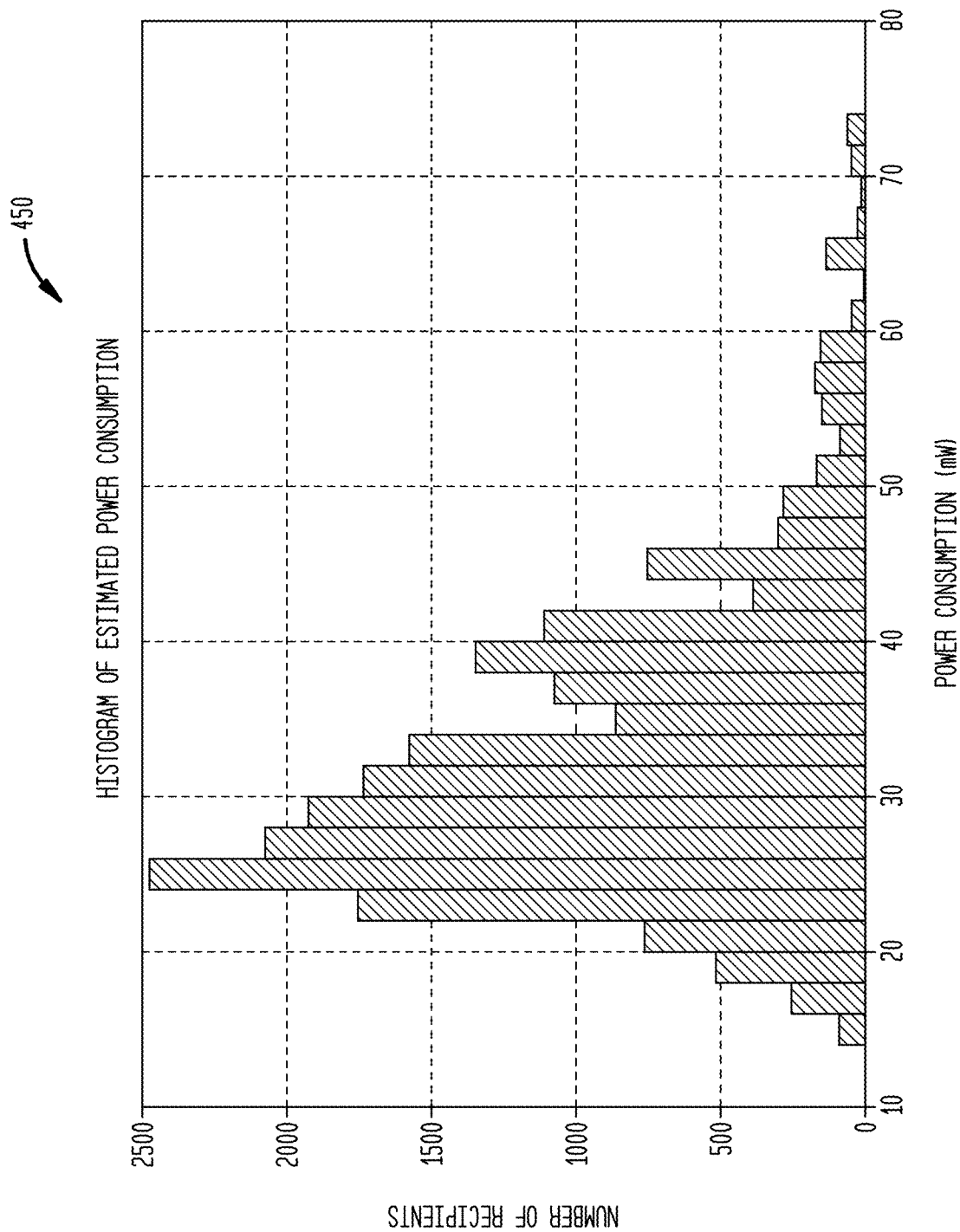
FIG. 4 is a diagram illustrating estimated power consumptions for a sample of recipients of a cochlear implant.

For example, FIG. 4 is a diagram 450 illustrating estimated power consumptions for a sample of recipients of a Cochlear® Nucleus® CP810 device. Cochlear® and Nucleus® are registered trademarks of Cochlear Limited. As can be seen in FIG. 4, a small number of the recipients have a daily cochlear implant system power consumption that exceeds fifty (50) Milliwatt (mW), while the majority of the recipients have a daily cochlear implant system power consumption of approximately 20-35 mW.

In general, the need for cochlear implant batteries to have sufficiently high capacities to meet the needs of recipients with large daily power consumption conflicts with the need to extend/increase the cycle life of integrated given rechargeable battery and, accordingly, the lifetime of a cochlear implant that includes the rechargeable battery. Presented herein are techniques for setting the cycle life of a rechargeable battery cell for a certain recipient based on the specific needs of the recipient. For example, the cycle life of a rechargeable battery cell may be improved (i.e., increased) for recipients that have lower daily power consumption needs. In other examples, the cycle life of a rechargeable monolithic battery cell may be decreased so as to provide maximum battery capacity for higher daily power consumption needs of other recipients.

More specifically, as described further below, the techniques presented herein set an end-of-charge voltage of a rechargeable battery of a particular cochlear implant (auditory prosthesis) based on an estimated power consumption of the cochlear implant, thereby allowing the battery capacity and cycle life balance to be catered to the needs of the specific recipient.

For ease of illustration, further details of the techniques presented herein are generally described with reference to cochlear implant 200 (FIG. 2) having a rechargeable battery 218. In certain examples, the rechargeable battery 218 has a maximum battery capacity of 200 mAh with a maximum end-of-charge voltage of 4.2 volts (V). Assuming that the rechargeable battery 218 is charged to 4.2 V, a battery capacity of 200 mAh will allow recipient's with a daily cochlear implant power consumption of approximately 46 mW to have an estimated battery life of approximately 16 hours. As used herein, the "estimated battery life" of a rechargeable battery is the estimated run-time of the rechargeable battery on a single complete/full charge, given (i.e., in view of) the estimated operational power requirements of the underlying device. That is, "battery life" is the time to discharge a fully charged battery under operating conditions to a defined end-of-discharge voltage or other criterion. It is to be appreciated that the use of these specific parameters are simply for purposes of illustration and that the techniques presented herein may be used with other types of rechargeable batteries, rechargeable batteries with different capacities, rechargeable batteries with different maximum end-of-charge voltages, etc. It is also to be appreciated that the techniques presented herein may be implemented in cochlear implant 300 of FIG. 3, other auditory prosthesis having different arrangements, or other electronic devices.

Figure 5:
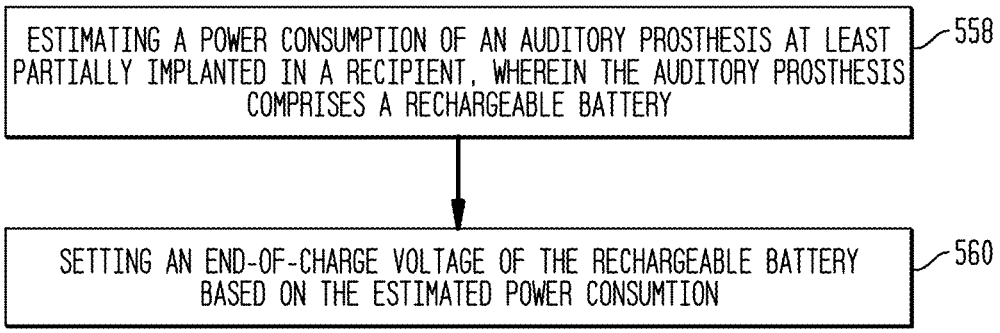
FIG. 5 is a flowchart of a method in accordance with embodiments presented herein.

FIG. 5 is a flowchart illustrating a method 556 in accordance with embodiments presented herein. As shown, method 556 begins at 558 where the power consumption of cochlear implant 200 is estimated. As noted, cochlear implant 200 includes a rechargeable battery 218. At 560, the end-of-charge voltage of the rechargeable battery 218 is set based on the estimated power consumption of the cochlear implant 200.

In accordance with embodiments presented herein, the power consumption of a cochlear implant, other auditory prosthesis, etc. may be determined in a number of different manners. FIG. 6 illustrates one example embodiment in which the power consumption of cochlear implant 200 is determined during a fitting session and is based on the recipient's operational map.

The effectiveness of cochlear implants and other auditory prostheses generally depends on how well a particular prosthesis is configured or "fitted" to the recipient of the particular prosthesis. For instance, the "fitting" of an auditory prosthesis to a recipient, sometimes also referred to as "programming" or "mapping," creates a set of recipient-specific operational settings (collectively and generally referred to as the recipient's "operational program" or "operational map") that define the specific operational characteristics of the hearing prosthesis to convert sound signals into electrical stimulation for delivery to the recipient. In the case of cochlear implants, fitting determines, among other parameters, the recipient's behavioral threshold levels (T-Level) at various stimulating contacts (i.e., the lower limit for electrical stimulation where the associated sound signals are barely audible to the recipient) and the recipient's behavioral comfort levels (C-Levels) at various stimulating contacts (i.e., the upper limit for electrical stimulation above which the associated sound signals are uncomfortably loud to the recipient). In accordance with certain embodiments presented herein, a recipient's operational map is used to estimate the power consumption of the cochlear implant. This estimate, in turn, is used to determine an appropriate end-of-charge voltage for the cochlear implant which, when fully charged, provides a capacity which is sufficient to satisfy the daily needs of the recipient, yet extends the life of the battery.

FIG. 6 illustrates a fitting system 670 that can be used to determine a recipient's operational map and to estimate the power consumption of cochlear implant 200. Fitting system 670 is, in general, a computing device that comprises a plurality of interfaces/ports 678(1)-678(N), a memory 680, a processor 684, and a user interface 686. The fitting system 670 may be a home-based clinical system for remote care or a system that remains in a clinical environment.

The interfaces 678(1)-678(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 6, interface 678(1) is connected to cochlear implant 200 having components implanted in a recipient 671. Interface 678(1) may be directly connected to the cochlear implant 200 or connected to an external device that is communication with the cochlear implant. Interface 678(1) may be configured to communicate with cochlear implant 200 via a wired or wireless connection (e.g., telemetry, Bluetooth, etc.).

The user interface 686 includes one or more output devices, such as a liquid crystal display (LCD) and a speaker, for presentation of visual or audible information to a clinician, audiologist, or other user. The user interface 686 may also comprise one or more input devices that include, for example, a keypad, keyboard, mouse, touchscreen, etc.

The memory 680 comprises fitting logic 681, power estimation logic 683, and end-of-charge voltage determination logic 685. Memory 680 may comprise read only memory (ROM), random access memory (RAM), magnetic disk storage media devices, optical storage media devices, flash memory devices, electrical, optical, or other physical/tangible memory storage devices. The processor 684 is, for example, a microprocessor or microcontroller that executes instructions for the fitting logic 681, power estimation logic 683, and end-of-charge voltage determination logic 685. Thus, in general, the memory 680 may comprise one or more tangible (non-transitory) computer readable storage media (e.g., a memory device) encoded with software comprising computer executable instructions and when the software is executed (by the processor 684) it is operable to perform the techniques described herein.

The fitting logic 681 may be executed to determine or update a recipient's operational map (i.e., the set of clinical parameters required for the operation of cochlear implant or other auditory prosthesis). The power estimation logic 683 is executed to measure the cochlear implant power consumption, given the recipient's operational map, by stimulating into an internal load of the implant. More specifically, the power consumption of the recipient's operational map is calculated by taking RF coil supply current ($I_{RF}$) measurements while stimulating into the internal load at the average comfort levels of the "N" (number of maxima) highest current electrodes. In certain examples, the accuracy of the current measurement ($I_{RF}$) is within +/−1.5 mA, under DC conditions, with all amplification gain settings, and in room temperature, with an accuracy of +/−3 mA for the full temperature range. In the case of an electro-acoustic device (i.e., an electro-acoustic operational map), an offset of an additional 2 mW is added. The internal load of the cochlear implant refers to a known resistive load in the cochlear implant which is internal to the implant integrated circuit (IC) which operates as an artificial or model (i.e., "dummy") electrode. Stimulating the internal load allows the implant to simulate stimulation without the recipient hearing any sounds.

Exemplary power consumption ($P_{SYS}$) calculations for an electro-acoustic operational map and a cochlear implant operational map are shown in detailed in Equations 1 and 2, respectively.

$$P_{SYS} = \frac{V_{Reg} \cdot I_{RF} + 4.8 + 2.2}{\eta} \qquad \text{Equation 1}$$

$$P_{SYS} = \frac{V_{Reg} \cdot I_{RF} + 4.8}{\eta} \qquad \text{Equation 2}$$

For a lithium ion battery, the $V_{Reg}$ (regulated output voltage of a voltage regulator) and $\eta$ are predetermined constants. $P_{SYS}$ is the estimated instantaneous maximum power consumption for the electro-acoustic prosthesis (Equation 1) or cochlear implant (Equation 2).

As noted elsewhere herein, it is to be appreciated that measurement of the cochlear implant power consumption, given the recipient's operational map, by stimulating into an internal load of the implant is one illustrative technique that be utilized in the techniques presented herein and the described techniques can be implemented using any of a variety of hardware configurations (i.e., embodiments of the present invention are not limited to utilizing this particular arrangement). That is, in general, it is to be appreciated that any suitable methods for determining power consumption (i.e., to compute end-of-charge voltage) can be implemented in accordance with embodiments presented herein, and that the used equations will largely be a function of context.

It is also to be appreciated that Equations 1 and 2, above, are examples of suitable relationships to determine power consumption calculations. It is to be appreciated that any of a number of different equations, algorithms, etc. can be implemented to compute a suitable end-of-charge voltage. More specifically, Equation 1 may be used in a situation where the approximate power consumed by the sound processor is 4.8 mW and an additional 2.2 mW is required for an electro-acoustic configuration. Equation 2 may be used for a non-electro-acoustic configurations (thus there is no 2.2 mW adjustment).

As noted, the clinical software uses the current measurements obtained from the cochlear implant 200 to derive the cochlear implant power consumption. The use of wireless accessories, mobile devices, or audio streaming causes an increase in the power consumption. The power consumption offset for audio streaming is under 9 mW to maintain acceptable performance, though the measured power consumption of these audio sources may be approximately an additional 5 mW for a wireless accessory, approximately an additional 6 mW for mobile device streaming, and an additional 7 mW for audio streaming.

Given the cochlear implant power consumption determined by the power estimation logic 683, the end-of-charge voltage determination logic 685 is configured to generate a battery life estimate (i.e., convert the cochlear implant power consumption into an estimated battery life using derived battery life equations). Based on this estimated battery life, the end-of-charge voltage determination logic 685 is configured to determine an appropriate end-of-charge voltage for rechargeable battery 218. As noted above, the estimated battery life of rechargeable battery 218 is the run-time of the rechargeable battery on a single complete/full charge, given (i.e., in view of) the estimated operational power requirements of the cochlear implant 200.

Different rechargeable batteries may have different derived equations for conversion of the power consumption into an estimated battery life. For example, the derived estimated battery life equation for one size and type of lithium ion battery may be given as shown below in Equation 3.

$$\text{Battery life(hours)} = 0.8 \times 369.63 \times P(\text{sys})^{-1.0285} \qquad \text{Equation 3:}$$

The derived battery life equation for another size of lithium ion battery may be given as shown below in Equation 4.

$$\text{Battery life(hours)} = 0.8 \times 752.7027 \times P(\text{sys})^{-1.0180} \qquad \text{Equation 4:}$$

As noted, Equations 3 and 4 relate to specific types of batteries (i.e., Equation 3 is relates to a compact lithium ion battery, while Equation 4 relates to a standard lithium ion battery). As such, it is to be appreciated that the above two equations for conversion of a power consumption estimate to an estimated battery life are merely illustrative and that other conversions may be used in embodiments of the present invention. In particular, implemented equations may be context dependent (e.g. based on the inherent battery characteristics).

As noted, the estimated battery life is, in general, a measurement of how long it takes to fully discharge battery 218 when it is fully charged, given the estimated power consumption of the cochlear implant 200. The capacity, and in turn the estimated battery life, of a rechargeable battery is affected by the end-of-charge voltage of the battery such that a reduction in the end-of-charge voltage decreases the battery capacity (and thus the estimated battery life) while an increase in the end-of-charge voltage increases the battery capacity (and thus the estimated battery life). However, in exchange for reducing the capacity of the battery, a reduction in the end-of-charge voltage has the benefit of increasing the cycle life of the battery. For example, lowering the end-of-charge voltage of a rechargeable battery from 4.2V to 4.1V (i.e., a 0.1V reduction) has the potential to double the cycle life, yet only reduces the battery capacity by approximately 10%. Conversely, an increase in the end-of-charge voltage has the decreases the cycle life of the battery.

As noted above, particularly with the rise of integrated cochlear implant batteries, there is a desire to extend the cycle life of these integrated batteries in order to extend the usable life of the cochlear implant or components thereof. Also as noted above, it is generally assumed that a recipient has the ability to charge his/her rechargeable battery 218 at night and, as such, the goal is to provide a recipient with approximately one full day of operation on a single battery charge (i.e., a fully charged battery should power the cochlear implant for at least approximately 14-16 hours). Therefore, the end-of-charge voltage determination logic 685 is configured to use the estimated battery life for rechargeable battery 218 to set an end-of-charge voltage for the rechargeable battery 218 that enables the rechargeable battery 218 to power the cochlear implant for approximately one day (e.g., approximately 14-16 hours), yet extends the cycle life of the rechargeable battery 218. This may include an increase or decrease in the end-of-charge voltage, depending on the needs of the recipient.

For example, in one arrangement, the end-of-charge voltage determination logic 685 determines that the power consumption of the cochlear implant 200, given the recipient's operational map, leads to a battery life estimate of approximately eighteen (18) hours. Since a battery life of 18 hours is more than is needed for one full day of operation (i.e., approximately 14-16 hours), the end-of-charge voltage of the battery 218 could be reduced, for example, from 4.2V to 4.1V (i.e., a 0.1V reduction). This leads to a reduced battery life (i.e., the extent of one charge cycle), but extends the cycle life of the rechargeable battery 218. In other words, the end-of-charge voltage determination logic 685 determines/selects a reduced end-of-charge voltage for the rechargeable battery 218 that allows the battery capacity to be tailored to the needs of the recipient while maximizing the cycle life of the rechargeable battery (i.e., balancing the capacity and cycle life based on the specific operational needs of the cochlear implant recipient).

In an alternative example, the end-of-charge voltage determination logic 685 determines that the power consumption of the cochlear implant 200, given the recipient's operational map, leads to a battery life estimate of approximately twelve (12) hours. Since a battery life of 20 hours is more than is needed for one full day of operation (i.e., approximately 14-16 hours), the end-of-charge voltage of the battery 218 could be increased, for example, from 3.9V to 4.2V (i.e., a 0.3V increased). This leads to an increased battery life (i.e., the extent of one charge cycle), but decreases the cycle life of the rechargeable battery 218. In other words, the end-of-charge voltage determination logic 685 determines/selects an increased end-of-charge voltage for the rechargeable battery 218 that allows the battery capacity to be tailored to the needs of the recipient at the expense of the cycle life of the rechargeable battery (i.e., balancing the capacity and cycle life based on the specific operational needs of the cochlear implant recipient).

As noted, embodiments have primarily described in the context of setting an end-of-charge voltage for a battery so as to provide one full day of charge. However, it is to be appreciated that this is illustrative and that techniques described herein can be implemented with respect to any suitable battery capacity (i.e., run-time duration).

The selection of a reduced end-of-charge voltage may occur in a number of different manners. In one example, different bins or groups of end-of-charge voltages are identified and associated with different classes of recipients that have similar power consumption characteristics. In these embodiments, a particular end-of-charge voltage is allocated to the cochlear implant based on the group with which the recipient is associated (e.g., based on power consumption). For example, a first end-of-charge voltage may be set for all recipients having power consumptions that exceed a first threshold, a second end-of-charge voltage may be set for all recipients having power consumptions that are below a second threshold, and a third end-of-charge voltage may be set for all recipients having power consumptions between the first and second thresholds (i.e., three groupings of recipients with high, medium, and low power consumptions). Other examples may use greater or fewer groupings of recipients and associated the end-of-charge voltages, or a continuous scale where any of a number of end-of-charge voltages that maximize cycle life while providing sufficient capacity can be selected.

In the example of FIG. 6, the determined end-of-charge voltage is sent to the cochlear implant 200. The cochlear implant 200, and more particularly the charge controller 214, configures/adjusts the adaptive battery charge circuitry 216 so that the rechargeable battery 218, when next recharged, will only be charged to the determined (e.g., reduced) end-of-charge voltage. That is, the charge controller 214 sets the end-of-charge voltage of the rechargeable battery 218 based on the estimated power consumption of the cochlear implant.

FIG. 6 has been described with reference to the generation of a power consumption estimate, the generation of a battery life estimate, and the determination of an end-of-charge voltage all by a fitting system that is in communication with a cochlear implant. It is to be appreciated that these embodiments are illustrative and that one or all of these operations could alternatively be performed by the cochlear implant or another device. For example, in one embodiment, the cochlear implant 200 is configured to receive information representing at least one of a power consumption of the cochlear implant 200 or an estimated battery life of the cochlear implant 200. The charge controller 214 (or other component of the cochlear implant 200) can use the received information to set the end-of-charge voltage for the rechargeable battery 218 that allows the battery capacity to be tailored to the needs of the recipient while maximizing the cycle life of the rechargeable battery. In other examples, the cochlear implant 200 includes functionality that is able to determine the estimated power consumption thereof and, in turn, use this information to determine and set the end-of-charge voltage for the rechargeable battery 218.

In other embodiments, the charge controller 214 is configured to monitor the recipient's power usage, over time, while the cochlear implant 200 is used by the recipient. Based on this monitoring, the charge controller 214 can slowly adjust the end-of-charge voltage voltage to reflect power usage trends identified by the charge controller. For example, if the recipient using the device more/less than expected, is being exposed to abnormally noisy/quiet environments for extended periods, etc., the charge controller 214 can detect that the cochlear implant 200 is using more or less power than expected. The charge controller 214 can then determine a new end-of-charge voltage for the rechargeable battery 200 based on this information and, accordingly, adjust the adaptive battery charge circuitry 216 so that the rechargeable battery 218, when next recharged, will only be charged to the newly determined end-of-charge voltage.

In other examples, the recipient could have some control over the end-of-charge voltage of the rechargeable battery 218. For example, a mobile phone or other electronic device may interface with the cochlear implant 200 that allows a user to select, approve, etc., a desired estimated battery life which can be converted to an end-of-charge voltage for the rechargeable battery 218. In still other embodiments, the cochlear implant 200 may include a user interface or other control mechanism that allows a user to select, approve, etc., an estimated battery life, and thus indirectly an end-of-charge voltage, for the rechargeable battery 218.

FIG. 6 also primarily illustrates an embodiment in which the end-of-charge voltage is reduced to extend the cycle life of a rechargeable battery. However, as noted above, it is to be appreciated that reduction of the end-of-charge voltage is illustrative and that, in certain embodiments, the techniques presented herein may increase the end-of-charge voltage. For example, a recipient may undergo a fitting process where a reduced end-of-charge voltage is selected. Over time, the recipient may determine that the reduced capacity resulting from the reduced end-of-charge voltage is insufficient to provide a full day of operation. As such, either at a subsequent fitting session, through an electronic device, the charge controller, or other control mechanism, the end-of-charge voltage could be increased to provide the recipient with more capacity. Such an increase need not result in a return to the maximum end-of-charge voltage of the battery.

As noted, power requirements can vary from recipient to recipient of cochlear implants and other auditory prostheses. However, a unique aspect of auditory prostheses, and cochlear implants in particular, is that, in general, the day-by-day power consumption of a particular recipient is relatively constant (e.g., compared with other consumer devices such as a mobile phone). As a result, once a power consumption estimate is performed, the typical daily needs of a particular recipient can be determined and used to adjust the end-of-charge voltage on a recipient-by-recipient basis.

Although embodiments have been primarily described with reference to auditory prostheses, it is to be appreciated that the techniques presented herein may be implanted in other implantable medical devices or other electronic devices with an integrated rechargeable battery and a power consumption that can be estimated.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
    obtaining information representative of a plurality of recipient-specific operational settings of an auditory prosthesis at least partially implanted in a recipient, wherein the auditory prosthesis comprises a rechargeable battery, adaptive battery charging circuitry, and a charge controller;
    determining, based on the plurality of recipient-specific operational settings, an estimate of anticipated operational power requirements of the auditory prosthesis when operating in accordance with the plurality of recipient-specific operational settings; and
    setting, using the charge controller and the adaptive battery charging circuitry, an end-of-charge voltage of the rechargeable battery based on the estimate of the anticipated operational power requirements of the auditory prosthesis.

2. The method of claim 1, wherein setting the end-of-charge voltage of the rechargeable battery further comprises:
    setting the end-of-charge voltage to a voltage level that provides a selected minimum cycle life for the rechargeable battery.

3. The method of claim 1, wherein setting the end-of-charge voltage of the rechargeable battery comprises:
    reducing the end-of-charge voltage of the rechargeable battery to a voltage level so as to reduce a capacity of the rechargeable battery, wherein the reduction in the end-of-charge voltage is selected based on the estimate of the anticipated operational power requirements of the auditory prosthesis.

4. The method of claim 1, wherein setting the end-of-charge voltage of the rechargeable battery comprises:
    increasing the end-of-charge voltage of the rechargeable battery to a voltage level so as to increase a capacity of the rechargeable battery, wherein the increase in the end-of-charge voltage is selected based on the anticipated operational power requirements of the auditory prosthesis.

5. The method of claim 1, further comprising:
    connecting the auditory prosthesis to a fitting system;
    performing, via the fitting system, one or more measurements at the auditory prosthesis;
    determining, based on the one or more measurements and the plurality of recipient-specific operational settings, the estimate of the anticipated operational power requirements of the auditory prosthesis when operating in accordance with the plurality of recipient-specific operational settings; and
    sending information representative of the estimate of the anticipated operational power requirements of the auditory prosthesis from the fitting system to the auditory prosthesis.

6. The method of claim 5, wherein performing the one or more measurements at the auditory prosthesis comprises:
    causing the auditory prosthesis to stimulate into an internal load of the auditory prosthesis to simulate delivery of stimulation to the recipient in accordance with one or more of the plurality of recipient-specific operational settings; and
    performing current measurements while the auditory prosthesis stimulates into the internal load.

7. The method of claim 1, wherein the plurality of recipient-specific operational settings include threshold and comfort levels for stimulation delivered to the recipient of the auditory prosthesis.

8. The method of claim 1, further comprising:
    receiving, at the auditory prosthesis, the information representative of a plurality of recipient-specific operational settings from a fitting system.

9. The method of claim 1, further comprising:
    generating an estimate of a battery life of the auditory prosthesis, wherein the estimate of the battery life is generated based on the estimate of the anticipated operational power requirements of the auditory prosthesis.

10. The method of claim 1, further comprising:
    monitoring power usage of the auditory prosthesis over a period of time; and
    adjusting the end-of-charge voltage of the rechargeable battery based on the monitored power usage.

11. The method of claim 1, wherein setting an end-of-charge voltage of the rechargeable battery based on the estimate of the anticipated operational power requirements of the auditory prosthesis, comprises:
    determining, based on the estimate of the anticipated operational power requirements of the auditory prosthesis, a selected termination voltage associated with charging of the rechargeable battery; and
    adjusting the adaptive battery charging circuitry so as to subsequently charge the rechargeable battery to the selected termination voltage.

12. The method of claim 1, wherein setting the end-of-charge voltage of the rechargeable battery based on the estimate of the anticipated operational power requirements of the auditory prosthesis, comprises:
    setting an end-of-charge voltage of the rechargeable battery based on an estimate of an anticipated total daily power requirements of the auditory prosthesis such that, when the rechargeable battery is fully charged and the auditory prosthesis operates in accordance with the plurality of recipient-specific operational settings, the rechargeable battery is expected to provide one full day of charge for the auditory prosthesis.

13. An implantable medical device system, comprising:
an implantable medical device, including a rechargeable battery, adaptive battery charging circuitry configured to charge the rechargeable battery, and a charge controller; and
one or more processors configured to:
obtain a recipient-specific operational map associated with a recipient's use of the implantable medical device, wherein the recipient-specific operational map defines specific operational characteristics of the implantable medical device for use in stimulating the recipient, and
determine, based on the recipient-specific operational map, an estimate of predicted operational power requirements of the implantable medical device when operating in accordance with the recipient-specific operational map,
wherein the charge controller is configured to set the adaptive battery charging circuitry based on the estimate of the predicted operational power requirements of the implantable medical device.

14. The implantable medical device system of claim 13, wherein the charge controller is further configured to set the adaptive battery charging circuitry in order to adapt an end-of-charge voltage associated with charging of the rechargeable battery to a voltage level that balances a capacity of the rechargeable battery and a cycle life of the rechargeable battery based on needs of the recipient.

15. The implantable medical device system of claim 14, wherein the charge controller is configured to set the adaptive battery charging circuitry in order to reduce the end-of-charge voltage associated with charging of the rechargeable battery to a voltage level that provides a selected minimum cycle life for the rechargeable battery.

16. The implantable medical device system of claim 13, wherein the one or more processors are part of a fitting system in communication with the implantable medical device and are further configured to:
perform one or more measurements at the implantable medical device;
determine, based on the one or more measurements, the estimate of the predicted operational power requirements of the implantable medical device; and
send information representative of the estimate of the predicted operational power requirements to the implantable medical device.

17. The implantable medical device system of claim 16, wherein to perform the one or more measurements, the fitting system is configured to:
cause the implantable medical device to stimulate into an internal load of the implantable medical device to simulate delivery of stimulation to the recipient; and
perform current measurements while the implantable medical device stimulates into the internal load.

18. The implantable medical device system of claim 16, wherein the information representative of the estimate of the predicted operational power requirements to the implantable medical device comprises the estimate of the predicted operational power requirements to the implantable medical device.

19. The implantable medical device system of claim 16, wherein the information representative of the estimate of the predicted operational power requirements to the implantable medical device comprises an estimate of a battery life of the implantable medical device, wherein the estimate of the battery life is generated based on the estimate of the predicted operational power requirements to the implantable medical device.

20. The implantable medical device system of claim 16, wherein the information representative of the estimate of the predicted operational power requirements to the implantable medical device comprises a selected end-of-charge voltage associated with charging of the rechargeable battery that is generated based on the estimate of the predicted operational power requirements of the implantable medical device.

21. The implantable medical device system of claim 13, wherein the implantable medical device is a totally implantable auditory prosthesis and the rechargeable battery is implanted in the recipient.

22. The implantable medical device system of claim 13, wherein the implantable medical device is an implantable auditory prosthesis that includes an external component, and wherein the rechargeable battery is integrated in the external component.

23. The implantable medical device system of claim 13, wherein the implantable medical device is a cochlear implant.

24. The implantable medical device system of claim 13, wherein to set the adaptive battery charging circuitry based on an estimate of the predicted operational power requirements of the implantable medical device, the charge controller is configured to:
set an end-of-charge voltage of the rechargeable battery based on an estimate of a predicted total daily power requirements of the implantable medical device such that, when the rechargeable battery is fully charged and the implantable medical device operates in accordance with the recipient-specific operational map, the rechargeable battery can provide one full day of charge for the implantable medical device.

* * * * *